United States Patent [19]

McGovern et al.

[11] Patent Number: 5,140,012

[45] Date of Patent: Aug. 18, 1992

[54] METHOD FOR PREVENTING ONSET OF RESTENOSIS AFTER ANGIOPLASTY EMPLOYING PRAVASTATIN

[75] Inventors: Mark E. McGovern, Philadelphia, Pa.; Miguel A. Ondetti, Princeton; Henry Y. Pan, Princeton Junction, both of N.J.

[73] Assignee: E. R. Squibb & Sons, Inc., Princeton, N.J.

[21] Appl. No.: 532,009

[22] Filed: May 31, 1990

[51] Int. Cl.$^5$ .................. A61K 37/02; C07K 5/06
[52] U.S. Cl. ........................ 514/19; 514/89; 514/91; 514/92; 514/94; 514/171; 514/212; 514/218; 514/223.5; 514/249; 514/255; 514/278; 514/318; 514/338; 514/343; 514/409; 514/422; 514/423; 514/533; 514/616; 514/693
[58] Field of Search ............ 514/19, 533, 89, 91, 514/92, 94, 171, 212, 218, 223.5, 249, 255, 278, 318, 338, 343, 409, 422, 423, 616, 693

[56] References Cited

U.S. PATENT DOCUMENTS 4,346,227  8/1982  Terahara et al. ............... 560/119

FOREIGN PATENT DOCUMENTS 0219782  11/1986  European Pat. Off. .

OTHER PUBLICATIONS

Gellman, J. et al., "Lovastatin, a HMG CoA Reductase Inhibitor, Reduces Restenosis Following Balloon Angioplasty in an Atherosclerotic Hypercholesterolemic Rabbit", Clinical Research, vol. 37, No. 2, 1989, p. 261A.
Clin. Res. 36, 1988: 259A.
Clin. Invest 83, 1985: 1419.
Clin. Res. 37, 1989: 286A.
Sahni, R. et al., "Prevention of Restenosis by Lovastatin", 62nd Scientific Sessions of the American Heart Assoc., New Orleans, Nov. 13-16, 1989, Circulation 80 (4 Suppl. 2) 1989, p. II-65.
Gellman, J. et al., "Lovastatin, a HMG CoA Reductase Inhibitor, Reduces Restenosis Following Balloon Angioplasty in an Atherosclerotic Hypercholesterolemic Rabbit", Clinical Research, vol. 37, No. 2, 1989, p. 261A.
Powell, J. S. et al., "Inhibitors of Angiotension-Converting Enzyme Prevent Myointimal Proliferation After Vascular Injury", Science, vol. 245, 186-188, Jul. 14, 1989.
Chobanian, A. V. et al., "Antiatherogenic Effect of Captopril in the Watanabe Heritable Hyperlipidemic Rabbit", Hypertension, vol. 15, No. 3, Mar. 1990, pp. 327-331.

Primary Examiner—Lester L. Lee
Attorney, Agent, or Firm—Burton Rodney

[57] ABSTRACT

A method is provided for preventing or reducing the risk of restenosis following angioplasty by administering pravastatin alone or in combination with an ACE inhibitor such as captopril or ceranapril, prior to, during and/or after angioplasty.

17 Claims, No Drawings

METHOD FOR PREVENTING ONSET OF RESTENOSIS AFTER ANGIOPLASTY EMPLOYING PRAVASTATIN

FIELD OF THE INVENTION

The present invention relates to a method for preventing onset of restenosis after angioplasty by administering an HMG CoA reductase inhibitor, which is pravastatin, alone or in combination with an ACE inhibitor, such as captopril or ceranapril.

BACKGROUND OF THE INVENTION

Percutaneous transluminal angioplasty (PTA), defined as any percutaneous transluminal method of decreasing stenosis within a blood vessel, whether caused by the existence of an atheromatous plaque, thrombosis, embolus, and/or mineral deposit, by any of a number of means such as balloon dilatation, thermal ablation, laser atherectomy, mechanical shaving, extraction, or ultrasonic pulverization, hereinafter referred to as angioplasty, is widely used in the treatment of occlusive vascular disease. However, it has been found that restenosis frequently occurs, and in the case of coronary angioplasty, restenosis occurs in about a third of cases within 6 months of the procedure.

Sahni, R., et al, "Prevention of Restenosis by Lovastatin," 62nd Scientific Sessions of the American Heart Association, New Orleans, Nov. 13–16 1989, Circulation 80 (4 Suppl. 2) 1989, p. II-65, disclose that lovastatin significantly reduces the incidence of restenosis following successful PTCA.

Gellman, J., et al, "Lovastatin, a HMG CoA Reductase Inhibitor, Reduces Restenosis Following Balloon Angioplasty in an Atherosclerotic Hypercholesterolemic Rabbit," Clinical Research, Vol. 37, No. 2, 1989, p. 261A, disclose that "lovastatin reduces total cholesterol and retards restenosis following balloon angioplasty in the hypercholesterolemic rabbit and merits evaluation in patients."

Pravastatin, also referred to as CS-514, an HMG CoA reducase inhibitor, is disclosed in U.S. Pat. No. 4,346,227.

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens discloses that ACE inhibition potentiates the action of bradykinin (a strong stimulator of prostacyclin release from endothelial cells) by inhibiting its degradation and ACE inhibitors, consequently, have an inhibitory effect on platelet aggregation.

Powell, J.S. et al "Inhibitors of Angiotension-Converting Enzyme Prevent Myointimal Proliferation After Vascular Injury," Science, Vol. 245, 186–188, Jul. 14, 1989, disclose that angiotensin-converting enzyme may participate in modulating the proliferative response of the vascular wall after arterial injury, and inhibition of this enzyme may have therapeutic applications to prevent the proliferative lesions that occur after coronary angioplasty and vascular surgery.

Other references which indicate that ACE inhibitors may prevent restenosis following angioplasty include "AII is Mitogenic for Endothelial Cells" (Clin. Res. 36, 1988:259A); "Exposure of Smooth Muscle Cells to AII Results in Expression of the Proto-Oncogene for PDGF" (J. Clin. Invest. 83, 1989:1419); "Cilazapril (and Captopril) Reduces the Myointimal Proliferation (Restenosis) in Rat Carotids Subjected to Balloon Angioplasty" (Clin. Res. 37, 1989:286A).

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[hydroxy(4-phenylbutyl)phosphinyl]oxy]-1-oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

DESCRIPTION OF THE INVENTION

In accordance with the present invention, a method is provided for preventing onset of or reducing risk of restenosis following angioplasty, wherein a therapeutically effective amount of pravastatin alone or in combination with an ACE inhibitor is administered systemically, such as orally or parenterally.

The pravastatin alone or in combination with the ACE inhibitor may be administered prior to, during and/or after the angioplasty procedure.

It is theorized that pravastatin reduces the incidence of restenosis by reducing serum cholesterol and by preventing cell proliferation.

The term "restenosis" as employed herein is as defined by Serruys, P. W., et al, "Incidence of restenosis after successful coronary angioplasty: a time related phenomenon. A quantitative angiographic study in 342 consecutive patients at 1, 2, 3, and 4 months," Circulation 1988; 7:361–71.

In preferred embodiments where the patient to be treated in accordance with the present invention is normotensive, the angiotensin converting enzyme inhibitor, where employed, will preferably be administered in amounts below that required to cause hemodynamic effects, that is below that required to cause a reduction in blood pressure.

The combination of the pravastatin and ACE inhibitor will be employed in a weight ratio to each other of within the range of from about 0.001:1 to about 1000:1 and preferably from about 0.05:1 to about 100:1.

The angiotensin converting enzyme inhibitor which may be employed herein preferably includes those containing a mercapto (-S-) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

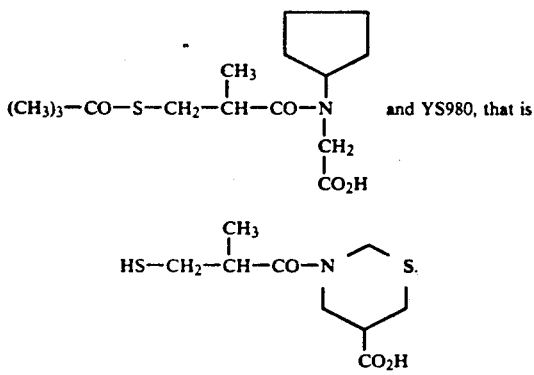

and YS980, that is

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (SQ 29,852 or ceranapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987 $R_o$31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2R(*)R(*)]]3R(*)]-2-[2-[1-(ethoxycarbonyl)-3-phenylpropyl]amino[-1-oxopropyl]-1,2,3,4-tetrahydro-6,7-dimethoxy-3-idoquinolinecarboxylic acid HCl) disclosed in Pharma-cologist 26:243, 266 (1984), WY-44221 (Wyeth) disclosed in J. Med. Chem. 26:394 (1983).

Preferred are those ACE inhibitors which are proline or substituted proline derivatives and most preferred are such ACE inhibitors which include a mercapto group.

The above-mentioned U.S. patents are incorporated herein by reference.

In carrying out the method of the present invention, pravastatin alone or in combination with an ACE inhibitor is administered to mammalian species, such as dogs, cats, humans, etc., prior to, during and/or after the angioplasty procedure, and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

Thus, for oral administration, a satisfactory result may be obtained employing the pravastatin in dosages employed, for example, for lovastatin as indicated in the Physician's Desk Reference, such as in an amount within the range of from about 1 to 2000 mg, and preferably from about 4 to about 200 mg.

A preferred oral dosage form, such as tablets or capsules, will contain pravastatin in an amount of from about 0.5 to about 100 mg, preferably from about 1 to about 80 mg, and more preferably from about 5 to about 40 mg.

With regard to the ACE inhibitor, for oral administration, a satisfactory result may be obtained employing the ACE inhibitor in an amount within the range of from about 0.01 mg/kg to about 100 mg/kg and preferably from about 0.1 mg/kg to about 5 mg/kg.

A preferred oral dosage form , such as tablets or capsules, will contain the ACE inhibitor in an amount of from about 0.1 to about 500 mg, preferably from about 2 to about 50 mg, and more preferably from about 5 to about 25 mg.

For parenteral administration, the ACE inhibitor will be employed in an amount within the range of from about 0.005 mg/kg to about 10 mg/kg and preferably from about 0.005 mg/kg to about 1.5 mg/kg.

Pravastatin and the ACE inhibitor may be employed together in the same oral dosage form or in separate oral dosage forms taken at the same time.

The compositions described above may be administered in the dosage forms as described above in single or divided doses of one to four times daily. It may be advisable to start a patient on a low dose and work up gradually to a high dose.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of the active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of pravastatin and ACE inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for weeks to 6 months or longer, beginning at the time of the angioplasty procedure. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

A pravastatin formulation in the form of tablets having the following composition was prepared as described below.

| Ingredient | Parts by Weight |
| --- | --- |
| Pravastatin | 7 |
| Lactose | 67 |
| Microcrystalline cellulose | 20 |

_-continued

| Ingredient | Parts by Weight |
| --- | --- |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 5 mg, 10 mg, 20 mg or 40 mg pravastatin which may be used in preventing restenosis following angioplasty.

EXAMPLES 2

Pravastatin tablets are prepared employing conventional pharmaceutical techniques containing 20 mg pravastatin and inert ingredients employed in lovastatin tablets, namely cellulose, color, lactose, magnesium stearate and starch and butylated hydroxyanisole as a preservative as described in the 1990 PDR.

The pravastatin tablets may be employed to prevent restenosis following angioplasty in accordance with the present invention.

EXAMPLE 3

A pravastatin tablet formulation is prepared as described in Example 1.

A captopril formulation suitable for oral administration together with pravastatin is prepared as described below.

1000 tablets each containing 100 mg of 1-[(2S)-3-mercapto-2-methylpropionyl]-L-proline were produced from the following ingredients.

| | |
| --- | --- |
| 1-[(2S)-3-Mercapto-2-methylpropionyl]-L-proline (captopril) | 7 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 7 mg of active ingredient.

The pravastatin tablets and captopril tablets may be administered as a combination in accordance with the teachings of the present invention to prevent restenosis following angioplasty. In addition, the pravastatin and captopril tablets may be ground up into powders and used together in a single capsule.

EXAMPLES 4

Pravastatin tablets are prepared as described in Example 2.

The pravastatin tablets may be employed in combination with enalapril tablets containing 7 mg enalapril and inactive ingredients as described in the 1990 PDR, in separate or combined dosage forms to prevent restenosis following angioplasty in accordance with the present invention.

What is claimed is:

1. A method for preventing or reducing the risk of restenosis following angioplasty, which comprises administering to a mammalian specie in need of such treatment an effective amount of pravastatin.

2. The method as defined in claim 1 wherein said pravastatin is administered in single or divided doses of from about 1 to about 2000 mg/one to four times daily.

3. The method as defined in claim 1 wherein the pravastatin is administered in single or divided doses of from about 4 to about 200 mg/one to four times daily.

4. The method as defined in claim 1 wherein the pravastatin is administered prior to angioplasty.

5. The method as defined in claim 1 wherein the pravastatin is administered during angioplasty.

6. The method as defined in claim 1 wherein the pravastatin is administered after angioplasty.

7. The method as defined in claim 1 wherein pravastatin is administered in combination with an ACE inhibitor.

8. The method as defined in claim 7 wherein the angiotensin converting enzyme inhibitor is a substituted proline derivative.

9. The method as defined in claim 7 wherein said angiotensin converting enzyme inhibitor includes a mercapto moiety and is a substituted proline derivative.

10. The method as defined in claim 7 wherein said angiotensin converting enzyme inhibitor is a substituted proline derivative.

11. The method as defined in claim 7 wherein said angiotensin converting enzyme inhibitor is captopril, zofenopril, enalapril, cernapril, fosinopril, lisinopril or fentiapril.

12. The method as defined in claim 7 wherein the angiotensin converting enzyme inhibitor is a phosphonate substituted amino or imino acid or salt thereof, a proline derivative, a substituted proline derivative, a mercaptoacyl derivative of a substituted proline, a carboxyalkyl dipeptide derivative, a phosphinylalkanoyl proline derivative or a phosphonamidate derivative.

13. The method as defined in claim 12 wherein said angiotensin converting enzyme inhibitor is a carboxyalkyl dipeptide derivative.

14. The method as defined in claim 7 wherein said angiotensin converting enzyme inhibitor is a phosphinylalkanoyl proline derivative, a phosphoramidate derivative, or a phosphonate substituted amino or imino acid or salt thereof.

15. The method as defined in claim 7 wherein the pravastatin is present in a weight ratio to said ACE inhibitor of the of within the range of from about 0.001:1 to about 1000:1.

16. The method as defined in claim 7 wherein said angiotensin converting enzyme inhibitor is administered in single or divided doses of from about 0.1 to about 500 mg/one to four times daily.

17. The method as defined in claim 7 wherein the ACE inhibitor is captopril, fosinopril or ceranapril.

* * * * *